United States Patent
Williams (10) Patent No.: US 10,390,835 B2
(45) Date of Patent: Aug. 27, 2019

(54) SURGICAL FASTENER APPARATUS WITH LINEAR POSITION SENSOR

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 362 days.

(21) Appl. No.: 15/355,187

(22) Filed: Nov. 18, 2016

(65) Prior Publication Data
US 2017/0164947 A1    Jun. 15, 2017

Related U.S. Application Data (60) Provisional application No. 62/265,480, filed on Dec. 10, 2015.

(51) Int. Cl.
| | | |
|---|---|---|
| *A61B 17/115* | (2006.01) | |
| *A61B 17/00* | (2006.01) | |
| *A61B 90/00* | (2016.01) | |

(52) U.S. Cl.
CPC . *A61B 17/1155* (2013.01); *A61B 2017/00022* (2013.01); *A61B 2017/00075* (2013.01); *A61B 2017/00115* (2013.01); *A61B 2017/00398* (2013.01); *A61B 2090/061* (2016.02); *A61B 2090/0811* (2016.02)

(58) Field of Classification Search
CPC ...... H02K 11/33; H02K 7/145; H01H 13/023; H01H 13/08; B25B 21/02; B25B 23/00; B25F 5/02
USPC ...................................................... 227/176.1
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev et al. | |
| 3,638,652 A | 2/1972 | Kelley | |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Extended European Search Report from Appl. No. 14181908.6 dated May 26, 2015.

(Continued)

*Primary Examiner* — Andrew M Tecco
*Assistant Examiner* — Praachi M Pathak (57) ABSTRACT

A fastener apparatus includes a handle, an elongate body connected to the handle, a fastener cartridge disposed adjacent the distal end of the elongate body and having at least one fastener, a pusher at least partially disposed within the elongate body, and adapted for longitudinal movement through a firing stroke to eject the at least one fastener from the fastener cartridge, a linear position sensor mounted within the elongate body and dimensioned and positioned to engage the pusher during movement through the firing stroke and being adapted to send at least one output signal representative of strain imparted thereupon by the pusher during the firing stroke, and a controller configured and adapted to determine a position of the pusher within the firing stroke based upon the at least one output signal.

15 Claims, 7 Drawing Sheets

(56) References Cited

U.S. PATENT DOCUMENTS

| | | | |
|---|---|---|---|
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |
| 4,319,576 | A | 3/1982 | Rothfuss |
| 4,350,160 | A | 9/1982 | Kolesov et al. |
| 4,351,466 | A | 9/1982 | Noiles |
| 4,379,457 | A | 4/1983 | Gravener et al. |
| 4,473,077 | A | 9/1984 | Noiles et al. |
| 4,476,863 | A | 10/1984 | Kanshin et al. |
| 4,485,817 | A | 12/1984 | Swiggett |
| 4,488,523 | A | 12/1984 | Shichman |
| 4,505,272 | A | 3/1985 | Utyamyshev et al. |
| 4,505,414 | A | 3/1985 | Filipi |
| 4,520,817 | A | 6/1985 | Green |
| 4,550,870 | A | 11/1985 | Krumme et al. |
| 4,573,468 | A | 3/1986 | Conta et al. |
| 4,576,167 | A | 3/1986 | Noiles |
| 4,592,354 | A | 6/1986 | Rothfuss |
| 4,603,693 | A | 8/1986 | Conta et al. |
| 4,606,343 | A | 8/1986 | Conta et al. |
| 4,632,290 | A | 12/1986 | Green et al. |
| 4,646,745 | A | 3/1987 | Noiles |
| 4,665,917 | A | 5/1987 | Clanton et al. |
| 4,667,673 | A | 5/1987 | Li |
| 4,671,445 | A | 6/1987 | Barker et al. |
| 4,700,703 | A | 10/1987 | Resnick et al. |
| 4,703,887 | A | 11/1987 | Clanton et al. |
| 4,708,141 | A | 11/1987 | Inoue et al. |
| 4,717,063 | A | 1/1988 | Ebihara |
| 4,752,024 | A | 6/1988 | Green et al. |
| 4,754,909 | A | 7/1988 | Barker et al. |
| 4,776,506 | A | 10/1988 | Green |
| 4,817,847 | A | 4/1989 | Redtenbacher et al. |
| 4,873,977 | A | 10/1989 | Avant et al. |
| 4,893,662 | A | 1/1990 | Gervasi |
| 4,903,697 | A | 2/1990 | Resnick et al. |
| 4,907,591 | A | 3/1990 | Vasconcellos et al. |
| 4,917,114 | A | 4/1990 | Green et al. |
| 4,957,499 | A | 9/1990 | Lipatov et al. |
| 4,962,877 | A | 10/1990 | Hervas |
| 5,005,749 | A | 4/1991 | Aranyi |
| 5,042,707 | A | 8/1991 | Taheri |
| 5,047,039 | A | 9/1991 | Avant et al. |
| 5,104,025 | A | 4/1992 | Main |
| 5,119,983 | A | 6/1992 | Green et al. |
| 5,122,156 | A | 6/1992 | Granger et al. |
| 5,139,513 | A | 8/1992 | Segato |
| 5,158,222 | A | 10/1992 | Green et al. |
| 5,188,638 | A | 2/1993 | Tzakis |
| 5,193,731 | A | 3/1993 | Aranyi |
| 5,197,648 | A | 3/1993 | Gingold |
| 5,197,649 | A | 3/1993 | Bessler et al. |
| 5,205,459 | A | 4/1993 | Brinkerhoff et al. |
| 5,221,036 | A | 6/1993 | Takase |
| 5,222,963 | A | 6/1993 | Brinkerhoff et al. |
| 5,253,793 | A | 10/1993 | Green et al. |
| 5,261,920 | A | 11/1993 | Main et al. |
| 5,271,543 | A | 12/1993 | Grant et al. |
| 5,271,544 | A | 12/1993 | Fox et al. |
| 5,275,322 | A | 1/1994 | Brinkerhoff et al. |
| 5,282,810 | A | 2/1994 | Allen et al. |
| 5,285,944 | A | 2/1994 | Green et al. |
| 5,285,945 | A | 2/1994 | Brinkerhoff et al. |
| 5,292,053 | A | 3/1994 | Bilotti et al. |
| 5,309,927 | A | 5/1994 | Welch |
| 5,312,024 | A | 5/1994 | Grant et al. |
| 5,314,435 | A | 5/1994 | Green et al. |
| 5,314,436 | A | 5/1994 | Wilk |
| 5,330,486 | A | 7/1994 | Wilk |
| 5,333,773 | A | 8/1994 | Main et al. |
| 5,344,059 | A | 9/1994 | Green et al. |
| 5,346,115 | A | 9/1994 | Perouse et al. |
| 5,348,259 | A | 9/1994 | Blanco et al. |
| 5,350,104 | A | 9/1994 | Main et al. |
| 5,355,897 | A | 10/1994 | Pietrafitta et al. |
| 5,360,154 | A | 11/1994 | Green |
| 5,368,215 | A | 11/1994 | Green et al. |
| 5,392,979 | A | 2/1995 | Green et al. |
| 5,395,030 | A | 3/1995 | Kuramoto et al. |
| 5,403,333 | A | 4/1995 | Kaster et al. |
| 5,404,870 | A | 4/1995 | Brinkerhoff et al. |
| 5,411,508 | A | 5/1995 | Bessler et al. |
| 5,425,738 | A | 6/1995 | Gustafson et al. |
| 5,433,721 | A | 7/1995 | Hooven et al. |
| 5,437,684 | A | 8/1995 | Calabrese et al. |
| 5,439,156 | A | 8/1995 | Grant et al. |
| 5,443,198 | A | 8/1995 | Viola et al. |
| 5,447,514 | A | 9/1995 | Gerry et al. |
| 5,454,825 | A | 10/1995 | Van Leeuwen et al. |
| 5,464,415 | A | 11/1995 | Chen |
| 5,470,006 | A | 11/1995 | Rodak |
| 5,474,223 | A | 12/1995 | Viola et al. |
| 5,497,934 | A | 3/1996 | Brady et al. |
| 5,503,635 | A | 4/1996 | Sauer et al. |
| 5,522,534 | A | 6/1996 | Viola et al. |
| 5,533,661 | A | 7/1996 | Main et al. |
| 5,588,579 | A | 12/1996 | Schnut et al. |
| 5,609,285 | A | 3/1997 | Grant et al. |
| 5,626,591 | A | 5/1997 | Kockerling et al. |
| 5,632,433 | A | 5/1997 | Grant et al. |
| 5,639,008 | A | 6/1997 | Gallagher et al. |
| 5,641,111 | A | 6/1997 | Ahrens et al. |
| 5,658,300 | A | 8/1997 | Bito et al. |
| 5,669,918 | A | 9/1997 | Balazs et al. |
| 5,685,474 | A | 11/1997 | Seeber |
| 5,709,335 | A | 1/1998 | Heck |
| 5,715,987 | A | 2/1998 | Kelley et al. |
| 5,718,360 | A | 2/1998 | Green et al. |
| 5,720,755 | A | 2/1998 | Dakov |
| 5,732,872 | A | 3/1998 | Bolduc et al. |
| 5,749,896 | A | 5/1998 | Cook |
| 5,758,814 | A | 6/1998 | Gallagher et al. |
| 5,799,857 | A | 9/1998 | Robertson et al. |
| 5,814,055 | A | 9/1998 | Knodel et al. |
| 5,833,698 | A | 11/1998 | Hinchliffe et al. |
| 5,836,503 | A | 11/1998 | Ehrenfels et al. |
| 5,839,639 | A | 11/1998 | Sauer et al. |
| 5,855,312 | A | 1/1999 | Toledano |
| 5,860,581 | A | 1/1999 | Robertson et al. |
| 5,868,760 | A | 2/1999 | McGuckin, Jr. |
| 5,881,943 | A | 3/1999 | Heck et al. |
| 5,915,616 | A | 6/1999 | Viola et al. |
| 5,947,363 | A | 9/1999 | Bolduc et al. |
| 5,951,576 | A | 9/1999 | Wakabayashi |
| 5,957,363 | A | 9/1999 | Heck |
| 5,993,468 | A | 11/1999 | Rygaard |
| 6,024,748 | A | 2/2000 | Manzo et al. |
| 6,050,472 | A | 4/2000 | Shibata |
| 6,053,390 | A | 4/2000 | Green et al. |
| 6,068,636 | A | 5/2000 | Chen |
| 6,083,241 | A | 7/2000 | Longo et al. |
| 6,102,271 | A | 8/2000 | Longo et al. |
| 6,117,148 | A | 9/2000 | Ravo et al. |
| 6,119,913 | A | 9/2000 | Adams et al. |
| 6,126,058 | A | 10/2000 | Adams et al. |
| 6,142,933 | A | 11/2000 | Longo et al. |
| 6,149,667 | A | 11/2000 | Hovland et al. |
| 6,176,413 | B1 | 1/2001 | Heck et al. |
| 6,179,195 | B1 | 1/2001 | Adams et al. |
| 6,193,129 | B1 | 2/2001 | Bittner et al. |
| 6,203,553 | B1 | 3/2001 | Robertson et al. |
| 6,209,773 | B1 | 4/2001 | Bolduc et al. |
| 6,241,140 | B1 | 6/2001 | Adams et al. |
| 6,253,984 | B1 | 7/2001 | Heck et al. |
| 6,258,107 | B1 | 7/2001 | Balazs et al. |
| 6,264,086 | B1 | 7/2001 | McGuckin, Jr. |
| 6,269,997 | B1 | 8/2001 | Balazs et al. |
| 6,273,897 | B1 | 8/2001 | Dalessandro et al. |
| 6,279,809 | B1 | 8/2001 | Nicolo |
| 6,302,311 | B1 | 10/2001 | Adams et al. |
| 6,338,737 | B1 | 1/2002 | Toledano |
| 6,343,731 | B1 | 2/2002 | Adams et al. |

(56) References Cited

U.S. PATENT DOCUMENTS

| | | |
|---|---|---|
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Willman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |

(56) References Cited

U.S. PATENT DOCUMENTS

| | | | |
|---|---|---|---|
| 7,922,743 B2 | 4/2011 | Heinrich et al. | |
| 7,931,183 B2 | 4/2011 | Orban, III | |
| 7,938,307 B2 | 5/2011 | Bettuchi | |
| 7,942,302 B2 | 5/2011 | Roby et al. | |
| 7,951,166 B2 | 5/2011 | Orban, III et al. | |
| 7,959,050 B2 | 6/2011 | Smith et al. | |
| 7,967,181 B2 | 6/2011 | Viola et al. | |
| 7,975,895 B2 | 7/2011 | Milliman | |
| 8,002,795 B2 * | 8/2011 | Beetel | A61B 17/068 606/219 |
| 8,006,701 B2 | 8/2011 | Bilotti et al. | |
| 8,006,889 B2 | 8/2011 | Adams et al. | |
| 8,011,551 B2 | 9/2011 | Marczyk et al. | |
| 8,011,554 B2 | 9/2011 | Milliman | |
| 8,016,177 B2 | 9/2011 | Bettuchi et al. | |
| 8,016,858 B2 | 9/2011 | Whitman | |
| 8,020,741 B2 | 9/2011 | Cole et al. | |
| 8,025,199 B2 | 9/2011 | Whitman et al. | |
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,096,458 B2 | 1/2012 | Hessler | |
| 8,109,426 B2 | 2/2012 | Milliman et al. | |
| 8,109,427 B2 | 2/2012 | Orban, III | |
| 8,113,406 B2 | 2/2012 | Holsten et al. | |
| 8,113,407 B2 | 2/2012 | Holsten et al. | |
| 8,123,103 B2 | 2/2012 | Milliman | |
| 8,128,645 B2 | 3/2012 | Sonnenschein et al. | |
| 8,132,703 B2 | 3/2012 | Milliman et al. | |
| 8,136,712 B2 | 3/2012 | Zingman | |
| 8,146,790 B2 | 4/2012 | Milliman | |
| 8,146,791 B2 | 4/2012 | Bettuchi et al. | |
| 8,181,838 B2 | 5/2012 | Milliman et al. | |
| 8,192,460 B2 | 6/2012 | Orban, III et al. | |
| 8,201,720 B2 | 6/2012 | Hessler | |
| 8,203,782 B2 | 6/2012 | Brueck et al. | |
| 8,211,130 B2 | 7/2012 | Viola | |
| 8,225,799 B2 | 7/2012 | Bettuchi | |
| 8,225,981 B2 | 7/2012 | Criscuolo et al. | |
| 8,231,041 B2 | 7/2012 | Marczyk et al. | |
| 8,231,042 B2 | 7/2012 | Hessler et al. | |
| 8,257,391 B2 | 9/2012 | Orban, III et al. | |
| 8,267,301 B2 | 9/2012 | Milliman et al. | |
| 8,272,552 B2 | 9/2012 | Holsten et al. | |
| 8,276,802 B2 | 10/2012 | Kostrzewski | |
| 8,281,975 B2 | 10/2012 | Criscuolo et al. | |
| 8,286,845 B2 | 10/2012 | Perry et al. | |
| 8,308,045 B2 | 11/2012 | Bettuchi et al. | |
| 8,312,885 B2 | 11/2012 | Bettuchi et al. | |
| 8,313,014 B2 | 11/2012 | Bettuchi | |
| 8,317,073 B2 | 11/2012 | Milliman et al. | |
| 8,317,074 B2 | 11/2012 | Ortiz et al. | |
| 8,322,590 B2 | 12/2012 | Patel et al. | |
| 8,328,060 B2 | 12/2012 | Jankowski et al. | |
| 8,328,062 B2 | 12/2012 | Viola | |
| 8,328,063 B2 | 12/2012 | Milliman et al. | |
| 8,343,185 B2 | 1/2013 | Milliman et al. | |
| 8,353,438 B2 | 1/2013 | Baxter, III et al. | |
| 8,353,439 B2 | 1/2013 | Baxter, III et al. | |
| 8,353,930 B2 | 1/2013 | Heinrich et al. | |
| 8,360,295 B2 | 1/2013 | Milliman et al. | |
| 8,365,974 B2 | 2/2013 | Milliman | |
| 8,403,942 B2 | 3/2013 | Milliman et al. | |
| 8,408,441 B2 | 4/2013 | Wenchell et al. | |
| 8,413,870 B2 | 4/2013 | Pastorelli et al. | |
| 8,413,872 B2 | 4/2013 | Patel | |
| 8,418,905 B2 | 4/2013 | Milliman | |
| 8,418,909 B2 | 4/2013 | Kostrzewski | |
| 8,424,535 B2 | 4/2013 | Hessler et al. | |
| 8,424,741 B2 | 4/2013 | McGuckin, Jr. et al. | |
| 8,430,291 B2 | 4/2013 | Heinrich et al. | |
| 8,430,292 B2 | 4/2013 | Patel et al. | |
| 8,453,910 B2 | 6/2013 | Bettuchi et al. | |
| 8,453,911 B2 | 6/2013 | Milliman et al. | |
| 8,485,414 B2 | 7/2013 | Criscuolo et al. | |
| 8,490,853 B2 | 7/2013 | Criscuolo et al. | |
| 8,511,533 B2 | 8/2013 | Viola et al. | |
| 8,551,138 B2 | 10/2013 | Orban, III et al. | |
| 8,567,655 B2 | 10/2013 | Nalagatla et al. | |
| 8,579,178 B2 | 11/2013 | Holsten et al. | |
| 8,590,763 B2 | 11/2013 | Milliman | |
| 8,590,764 B2 | 11/2013 | Hartwick et al. | |
| 8,608,047 B2 | 12/2013 | Holsten et al. | |
| 8,616,428 B2 | 12/2013 | Milliman et al. | |
| 8,616,429 B2 | 12/2013 | Viola | |
| 8,622,275 B2 | 1/2014 | Baxter, III et al. | |
| 8,631,993 B2 | 1/2014 | Kostrzewski | |
| 8,636,187 B2 | 1/2014 | Hueil et al. | |
| 8,640,940 B2 | 2/2014 | Ohdaira | |
| 8,662,370 B2 | 3/2014 | Takei | |
| 8,663,258 B2 | 3/2014 | Bettuchi et al. | |
| 8,672,931 B2 | 3/2014 | Goldboss et al. | |
| 8,678,264 B2 | 3/2014 | Racenet et al. | |
| 8,684,248 B2 | 4/2014 | Milliman | |
| 8,684,250 B2 | 4/2014 | Bettuchi et al. | |
| 8,684,251 B2 | 4/2014 | Rebuffat et al. | |
| 8,684,252 B2 | 4/2014 | Patel et al. | |
| 8,733,611 B2 | 5/2014 | Milliman | |
| 8,893,946 B2 * | 11/2014 | Boudreaux | A61B 17/068 227/175.1 |
| 2003/0111507 A1 | 6/2003 | Nunez | |
| 2004/0073090 A1 | 4/2004 | Butler et al. | |
| 2005/0051597 A1 | 3/2005 | Toledano | |
| 2005/0107813 A1 | 5/2005 | Gilete Garcia | |
| 2006/0000869 A1 | 1/2006 | Fontayne | |
| 2006/0011698 A1 | 1/2006 | Okada et al. | |
| 2006/0201989 A1 | 9/2006 | Ojeda | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2009/0206144 A1 * | 8/2009 | Doll | A61B 17/07207 227/177.1 |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2010/0019016 A1 | 1/2010 | Edoga et al. | |
| 2010/0051668 A1 | 3/2010 | Milliman et al. | |
| 2010/0084453 A1 | 4/2010 | Hu | |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0258611 A1 | 10/2010 | Smith et al. | |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0114697 A1 | 5/2011 | Baxter, III et al. | |
| 2011/0114700 A1 | 5/2011 | Baxter, III et al. | |
| 2011/0144640 A1 | 6/2011 | Heinrich et al. | |
| 2011/0147432 A1 | 6/2011 | Heinrich et al. | |
| 2011/0192882 A1 | 8/2011 | Hess et al. | |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0056516 A1 | 3/2013 | Viola | |
| 2013/0060258 A1 | 3/2013 | Giacomantonio | |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0126580 A1 | 5/2013 | Smith et al. | |
| 2013/0153630 A1 | 6/2013 | Miller et al. | |
| 2013/0153631 A1 | 6/2013 | Vasudevan et al. | |
| 2013/0153633 A1 | 6/2013 | Casasanta, Jr. et al. | |

(56) References Cited

U.S. PATENT DOCUMENTS

| | | |
|---|---|---|
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2015/0157321 A1* | 6/2015 | Zergiebel ......... A61B 17/07207 227/175.1 |
| 2015/0209035 A1* | 7/2015 | Zemlok ............ G01D 18/008 73/1.01 |
| 2015/0316431 A1* | 11/2015 | Collins ............. A61B 90/98 606/219 |
| 2015/0351765 A1* | 12/2015 | Valentine ........ A61B 17/07207 227/176.1 |
| 2016/0066916 A1* | 3/2016 | Overmyer ........... A61B 17/105 227/176.1 |
| 2016/0374668 A1* | 12/2016 | Measamer ........... A61B 17/068 227/175.1 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| ES | 2370139 T3 | 12/2011 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2008/107918 A1 | 9/2008 |
| WO | 2015157147 A1 | 10/2015 |

OTHER PUBLICATIONS

European Examination Report from Appl. No. 14181908.6 dated May 3, 2016.

European Search Report in connection with European Application No. 16203295, dated Feb. 20, 2017, 7 pages.

* cited by examiner

SURGICAL FASTENER APPARATUS WITH LINEAR POSITION SENSOR

CROSS-REFERENCE TO RELATED APPLICATIONS

This application claims the benefit of and priority to U.S. Provisional Patent Application No. 62/265,480 filed Dec. 10, 2015, the entire disclosure of which is incorporated by reference herein.

BACKGROUND

1. Technical Field

The present disclosure relates to a surgical fastener apparatus for applying surgical fasteners to body tissue and, more particularly, relates to a surgical fastener apparatus incorporating a linear position sensor adapted for determining the location of the pusher of the fastener instrument during movement through its firing stroke.

2. Description of Related Art

Anastomosis refers to the surgical joining of separate tissue sections. An anastomosis procedure may follow surgery in which a diseased or defective section of a hollow tissue or organ structure is removed, thus requiring the joining of the remaining sections of the tissue. Depending on the particular procedure performed and/or other factors, the end sections of the tissue may be joined by linear anastomosis or circular anastomosis, e.g., end-to-end anastomosis, end-to-side anastomosis, or side-to-side anastomosis.

A fastener instrument or apparatus adapted for anastomosis generally includes a pusher or drive mechanism which, during a firing stroke, delivers an array of fasteners or staples through each of two sections of tissue to join the tissue sections, and may simultaneously cut or core adjoining tissue within the newly joined sections to separate or clear a passage therethrough. To ensure that the firing stroke effectively drive the staples or fasteners through tissue to achieve successful anastomosis of the tissue sections, confirmation of the location of the pusher relative to the fasteners during the firing stroke would be of significant value to the clinician. The size of the staple or fastener utilized during the procedure, the thickness of the tissue and/or manufacturing tolerances of the firing components of the instrument will affect travel of the pusher, and may detract from the overall effectiveness of the anastomosis. This issue becomes even more critical with reusable instruments having a reusable handle adapted for use with various loading units with mounted end effectors. Variations in the dimensions of the drive components of the loading units and end effectors, and/or size of the fasteners will impact the effectiveness of the firing stroke.

SUMMARY

Accordingly, the present disclosure is directed to further improvements in fastener apparatuses. In accordance with the present disclosure, a fastener apparatus includes a handle, an elongate body connected to the handle, a fastener cartridge having at least one fastener, a pusher at least partially disposed within the elongate body, and being adapted for longitudinal movement through a firing stroke to eject the at least one fastener from the fastener cartridge, a linear position sensor mounted within the elongate body and dimensioned and positioned to engage the pusher during movement through the firing stroke, and being adapted to send at least one output signal representative of strain imparted thereupon by the pusher during the firing stroke, and a controller configured and adapted to determine a position of the pusher within the firing stroke based upon the at least one output signal.

In one aspect, the controller includes a memory for storing calibration data associated with the strain imparted on the linear position sensor by the pusher at a plurality of positions of the pusher during the firing stroke. The controller may be configured to compare the at least one output signal to the calibration data to determine the position of the pusher within the firing stroke.

The linear position sensor may include a spring member dimensioned to be engaged by the pusher during movement through the firing stroke and a strain gauge mounted to the spring member. The strain gauge is adapted to send the at least one output signal. In one embodiment, the spring member is a leaf spring mounted within the elongate body in cantilever relation.

The pusher may include a sensor contact surface for engaging the spring member. The sensor contact surface is positioned to engage the spring member upon movement of the pusher during the firing stroke.

The fastener apparatus may include a motor operably coupled to the pusher for controlling movement of the pusher. The controller may be configured to control operation of the motor based upon the at least one output signal sent by the linear position sensor. An input device may be provided to enter or input data for storing by the memory. The input data may include one of the calibration data, a size of the at least one fastener, tissue type or biographical data of a subject. The controller may be configured to control at least one parameter of operation of the motor based upon the input data.

The fastener apparatus may further include at least one feedback sensor to monitor a load condition of the motor. A visual display for displaying visual indicia corresponding to the position of the pusher during the firing stroke may be provided. An audio output is also contemplated.

In one aspect, the fastener cartridge includes a plurality of fasteners arranged in an annular array and further includes an anvil mountable relative to the fastener cartridge. The anvil includes an anvil head dimensioned for forming or crimping the fasteners.

In another aspect of the present disclosure, a sensor system for use with a surgical apparatus of the type having at least one pusher adapted to travel through a firing stroke includes a linear position sensor and a controller (e.g., a microcontroller). The linear position sensor is mountable within the surgical apparatus and is dimensioned and positioned to engage the pusher during movement through the firing stroke. The linear position sensor is adapted to send at least one output signal to the controller representative of strain imparted thereupon by the pusher during the firing stroke. The controller is configured and adapted to determine a position of the pusher within the firing stroke based upon the at least one output signal and calibration data stored within the memory of the controller.

The linear position sensor may include a spring member dimensioned to be engaged by the pusher during movement through the firing stroke and a strain gauge mounted to the spring member. The strain gauge is adapted to send the at least one output signal to the controller.

The linear position sensor of the present disclosure provides valuable information to the clinician pertaining to the location of the pusher relative to the fastener cartridge and/or the fasteners during the firing stroke. Based on this information, the potential that the firing stroke will be successful is greatly improved. In addition, the linear position sensor accommodates for any variations in manufacturing tolerances, tool types and fastener sizes, and with the calibration data and associated computer logic incorporated within the controller, the appropriate length or distance of the firing stroke of the pusher can be determined and controlled to achieve, e.g., successful anastomosis of tissue sections.

Other advantages of the present disclosure will become apparent from the following description and accompanying drawings.

BRIEF DESCRIPTION OF THE DRAWINGS

Embodiments of the present disclosure will be appreciated by reference to the accompanying drawings wherein.

DETAILED DESCRIPTION

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

The sensor assembly including the linear position sensor of the present disclosure may be incorporated within any surgical instrument or apparatus of the type having a pusher adapted to travel through a pusher or firing stroke. In the description to follow, the sensor assembly is discussed in combination with a circular anastomosis apparatus; however, it is envisioned that the sensor assembly may be incorporated within various types of instruments including linear stapling devices, laparoscopic staplers, open staplers, or skin staplers, or with instruments which do not deploy fasteners such as surgical graspers, forceps, biopsy devices, etc.

Figure 1:
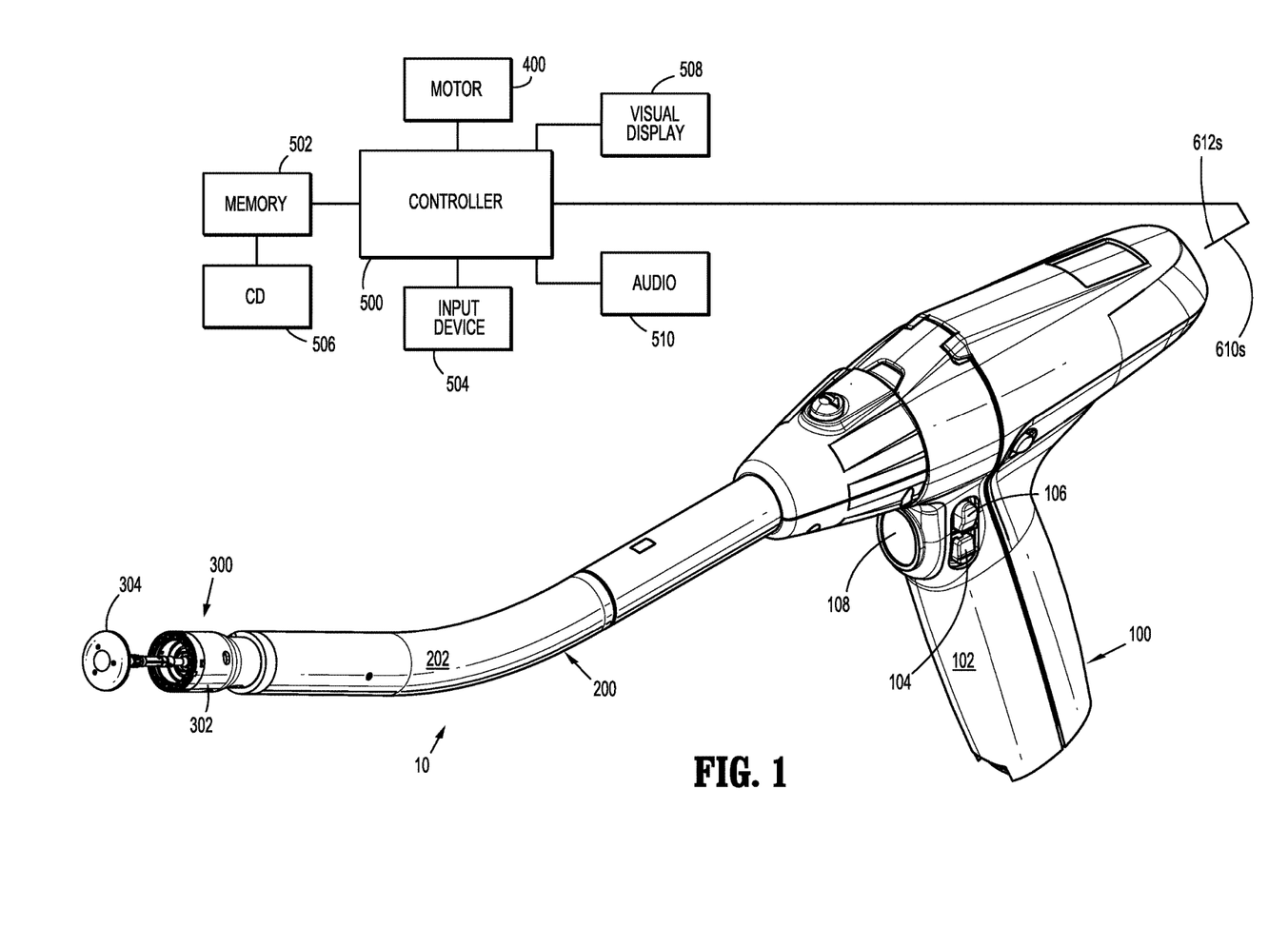
FIG. 1 is a perspective view of a fastener apparatus illustrating the handle, the elongate tool with mounted end effector and components associated with the sensor assembly and controller for controlling operation of the fastener apparatus.

Referring now to the drawings where like reference numerals indicate similar components throughout the several views, FIG. 1 illustrates the surgical fastener apparatus 10 in accordance with the principles of the present disclosure. The surgical fastener apparatus 10 may be adapted to apply an annular or circular array of fasteners or staples to tissue in connection with an end-to-end or circular anastomosis of tissue. However, the fastener apparatus 10 may be adapted to apply one or more linear rows of fasteners or staples. The fastener apparatus 10 includes a handle 100, an elongate body or tool 200 connectable to the handle 100 and an end effector 300. The handle 100 may be any handle assembly (reusable or disposable) having a handle frame 102 and at least one actuator, and in some embodiments, two or more actuators 104, 106, 108 adapted to control operation of the fastener apparatus 10. The handle 100 may be powered, e.g., an electromechanical handle, incorporating a motor 400 and a controller 500 having associated logic, software or circuitry to control operation of the motor 400, and, in turn, control movement of the end effector 300. The actuators 104, 106, 108 may communicate with the controller 500 to control operation of the motor 400 and the various pusher or drive components within the handle frame 102. In the alternative, the handle 100 may be mechanically activated, e.g., devoid of a motor, whereby the end effector 300 is controlled through mechanical linkages, gears or the like. Further details of a suitable handle for use with the fastener apparatus 10 may be ascertained by reference to commonly assigned U.S. Patent Publication No. 2011/0121049 to Malinouskas et al. or U.S. Patent Publication No. 2013/0214025 to Zemlock et al., the entire contents of each document being incorporated by reference herein.

The elongate tool 200 may be a single use loading unit (SULU) or a multi-use loading unit (MULU) having the end effector 300, which in one embodiment, is adapted, e.g., for single or multiple firing of one or more fasteners. All or a portion of the elongate tool 200 and the end effector 300 may be reusable with the reusable components subject to sterilization procedures after use.

The end effector 300 may be a fastener firing effector adapted to fire a circular or annular array of fasteners. In accordance with this embodiment, the end effector includes a staple or fastener cartridge 302 and an anvil 304. The fastener cartridge 302 may be mounted to, or a component of, the elongate tool 200, and houses at least one fastener or a plurality of fasteners. In the alternative, the fastener cartridge 302 may be releasably mounted to the elongate tool 200, and replaced with another fastener cartridge 302 upon exhaustion of the supply of fasteners. The anvil 304 may be releasably mountable relative to the fastener cartridge 302. When coupled to the elongate tool 200, the anvil 304 is movable relative to the fastener cartridge 302 between open and approximated positions. The fasteners are driven from the fastener cartridge 302 through tissue positioned about the components, and crimped by the anvil 304. Further details of the end effector 300 may be ascertained by reference to commonly assigned U.S. Patent Publication No. 2015/0014393 to Milliman, the entire contents of which are incorporated by reference herein.

Figure 2:
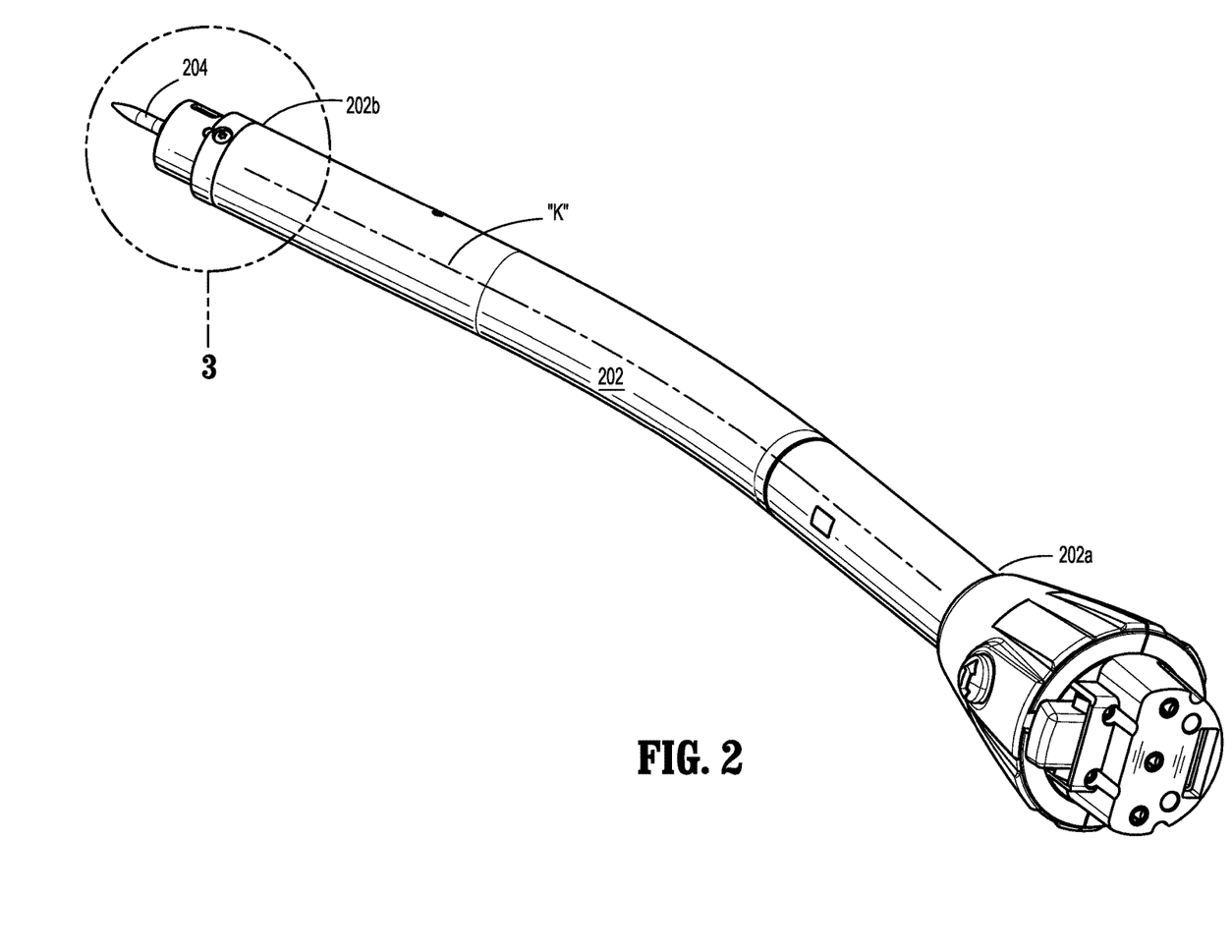
FIG. 2 is a perspective view of the elongate tool with the anvil of the end effector removed.

Referring now to FIGS. 1-2, the elongate tool 200 includes an outer body or shell 202 which houses the components of the fastener firing mechanism for firing the fasteners and the components of the approximating mechanism for approximating the anvil 304 and the fastener cartridge 302. The outer body 202 defines proximal or trailing and distal or leading ends 202a, 202b, and defines longitudinal axis "k". The elongate tool 200 further includes an anvil retainer or trocar 204 which is releasably mounted to the outer body 202 and relative to the fastener cartridge 302. FIG. 2 illustrates the elongate tool 200 released from the handle frame 102 of the handle 100. In FIG. 2, the fastener cartridge 302 is shown removed (for illustrative purposes) from the outer body 202 of the elongate tool 200. The anvil retainer 204 secures and/or mounts the anvil 304 relative to the fastener cartridge 302, and may function as a trocar assisting in advancing the elongate tool 200 through tissue in the absence of the mounted anvil 304.

Figures 3, 4, 5:
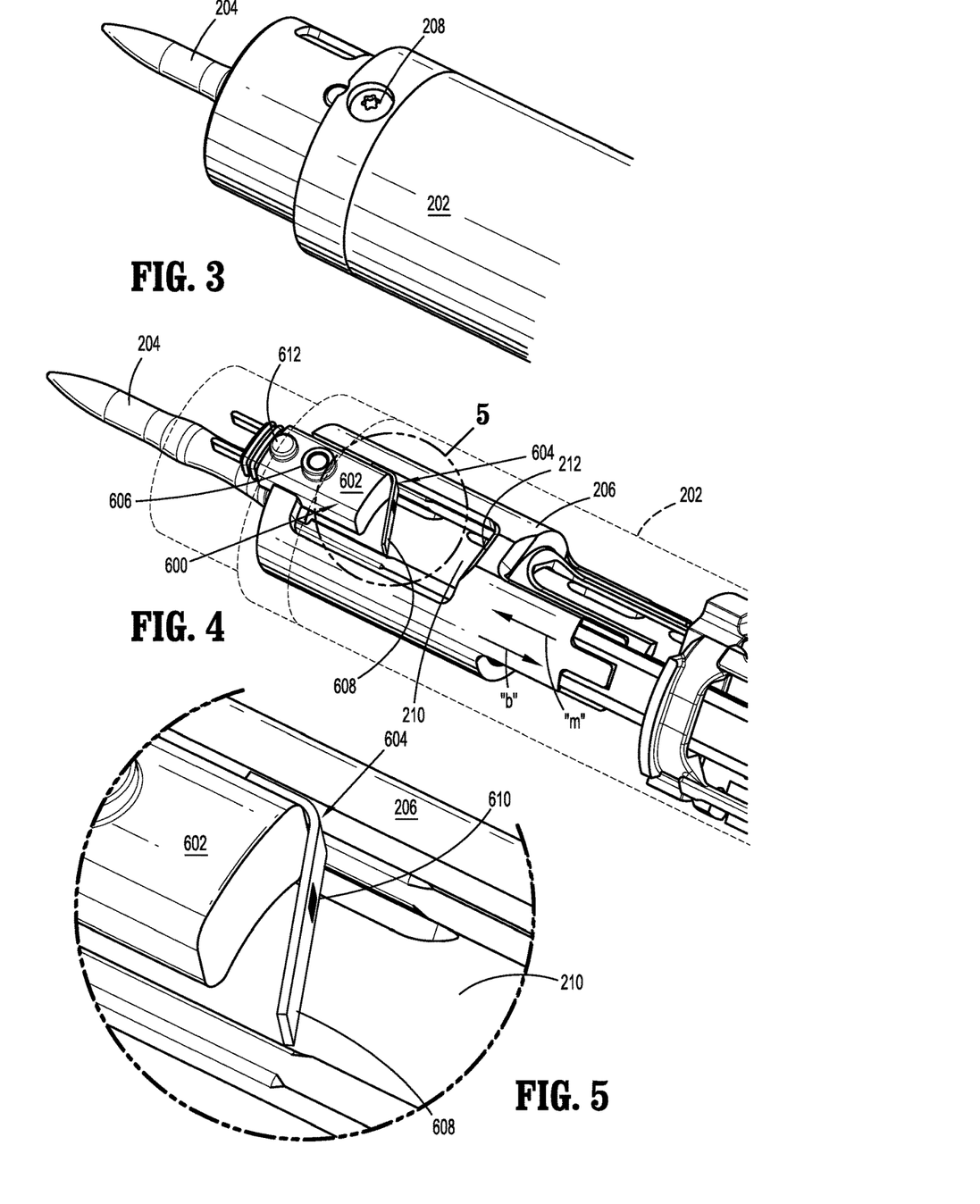
FIG. 3 is an enlarged isolated view of the area of detail identified in FIG. 2.
FIG. 4 is a perspective view of the distal end of the elongate tool illustrating the pusher and the linear position sensor of the sensor assembly mounted within the outer body (in phantom) of the elongate tool.
FIG. 5 is an enlarged isolated view of the area of detail identified in FIG. 4.

Referring now to FIGS. 3-5, the fastener apparatus 10 includes a sensor assembly 600 which may be mounted within the elongate tool 200 or, alternatively, within the end effector 300. In one embodiment, the sensor assembly 600 is mounted within the elongate tool 200 adjacent the pusher 206 of the elongate tool 200. The sensor assembly 600 includes a sensor mount 602 and a linear position sensor, identified generally as reference numeral 604. The sensor mount 602 is secured in fixed relation to the outer body 202 of the elongate tool 200 via a fastener such as a screw 208 which extends through the outer body 202 and is received within a threaded opening 606 of the sensor mount 602. Other mechanisms for securing the sensor assembly 600 relative to the outer body 202 are also envisioned.

The linear position sensor 604 is adapted to send at least one signal, e.g., a plurality of signals, to the controller 500 corresponding to the position(s) of the pusher 206 of the elongate tool 200 during the firing stroke of the pusher 206. The linear position sensor 604 includes a spring 608 and a strain gauge 610 secured to the spring 608. The spring 608 may be a leaf spring mounted in cantilevered relation to the sensor mount 602 through any conventional means including adhesives and/or fasteners. The strain gauge 610 may be any conventional gauge, incorporating, e.g., one or more Wheatstone bridge(s), adapted to measure strain imparted thereupon by an object, e.g., the pusher 206 of the fastener apparatus 10. The strain gauge 610 may be secured to the spring 608 with an adhesive or the like. The strain gauge 610 is in electrical communication with the controller 500 and is configured and adapted to send signals to the controller during operation of the fastener apparatus 10.

The sensor assembly 600 is adapted for slidable movement relative to the pusher 206 of the elongate tool 200. In one embodiment, the pusher 206 incorporates a recess or opening 210 which at least partially accommodates the sensor mount 602. The sensor mount 602 is adapted to traverse the opening 210 during the firing and return strokes (represented by directional arrows "m", "b", respectively of FIG. 3) of the pusher 206. Any means for permitting sliding movement of the sensor mount 602 relative to the pusher 206 are envisioned including, e.g. with the use of rails, grooves the like.

The pusher 206 further incorporates a sensor contact surface 212 which engages the linear position sensor 604 during the firing stroke of the pusher 206. The sensor contact surface 212 of the pusher 206 may be spaced from the sensor mount 602 when in an in an initial unactuated condition depicted in FIGS. 4 and 5, due to manufacturing tolerances, the structural and functional features of the selected elongate tool 200, etc., permitting free travel of the pusher 206 prior to engagement with the linear position sensor 604. Any initial free travel of the pusher 206 is not critical to the effectiveness of the fastener apparatus 10 in firing fasteners and achieving anastomosis. As to be appreciated, the linear position sensor 604 when engaged by the pusher 206 provides, e.g., a continuous indication to the clinician of the location of the pusher 206 relative to the fastener cartridge 302 and the fasteners during the firing stroke. This information assists the clinician by providing confirmation of the location of the pusher 206 and completion of the firing stroke.

As a further option, the sensor assembly 600 may include one or more feedback sensors, represented generally as reference numeral 612 in communication with the end effector 300 and/or the pusher 206. The feedback sensor 612 may be any sensor configured to measure current, voltage, temperature and/or force (an additional strain gauge or load cell) to assist in determining the load placed on the motor 400 during operation of the fastener apparatus 10. The feedback sensor(s) 612 is/are also in electrical communication with the controller 500 and may assist in detecting abnormal loads, e.g., outside a predetermined load range, indicating a potential problem with the functioning of the fastener apparatus 10 and/or the clamped tissue, which is communicated to the controller 500.

With reference again to FIG. 1, the controller 500 may be a microcontroller incorporated within the apparatus 10, e.g., within the handle 100 of the apparatus 10, or may be external to the fastener apparatus 10. The controller 500 includes memory or storage 502 for storing data which may be entered, inputted or collected through input device 504. The memory or storage 502 incorporates calibration data (CD) 506 of the linear position sensor 604 which is ascertained prior to use of the fastener apparatus 10. The calibration data 506 includes the position of the pusher 206 and corresponding force or strain exerted on the strain gauge 610 taken or calculated at a plurality of positions of the pusher 206 during the firing stroke. This information or data will provide the clinician with an indication of the position of the pusher 206 during the firing stroke based on the detected strain on the strain gauge 610, and thus will assist in ensuring that the pusher 206 advances or travels through the desired distance to ensure effective anastomosis of the tissue. A visual display 508 may be in communication with the controller 500 to provide either a graphical or numerical readout (or any other visual indicia) of the location of the pusher 206 to further assist the clinician. The visual display 508 may also provide visual indicia of various operating parameters based on feedback, e.g., one or more signals, received from the feedback sensor 612. An audio output 510 (including, e.g., tones, bells, buzzers, integrated speaker, etc.) is also contemplated. The audio output 510 can be used in conjunction with, or in lieu of, the visual display 508.

The use of the sensor assembly 600 with the fastener apparatus 10 will now be described. Prior to use, the linear position sensor 604 of the fastener apparatus 10 is calibrated, and the calibration data 506 is entered via the input device 504 into the memory 502 associated with the controller 500. Other data may be entered via the input device 504 for subsequent processing by the controller 500, including biographical data of the patient, fastener or staple size, type of elongate tool 200, tissue characteristics, etc. Based on the calibration data 506 and/or the other input data, the controller 500 may select a specific program of operation of the fastener apparatus 10.

Upon completion of data input, the tissue sections are positioned about the anvil 304 and the fastener cartridge 302 as is conventional with a circular anastomosis procedure.

Figure 6:
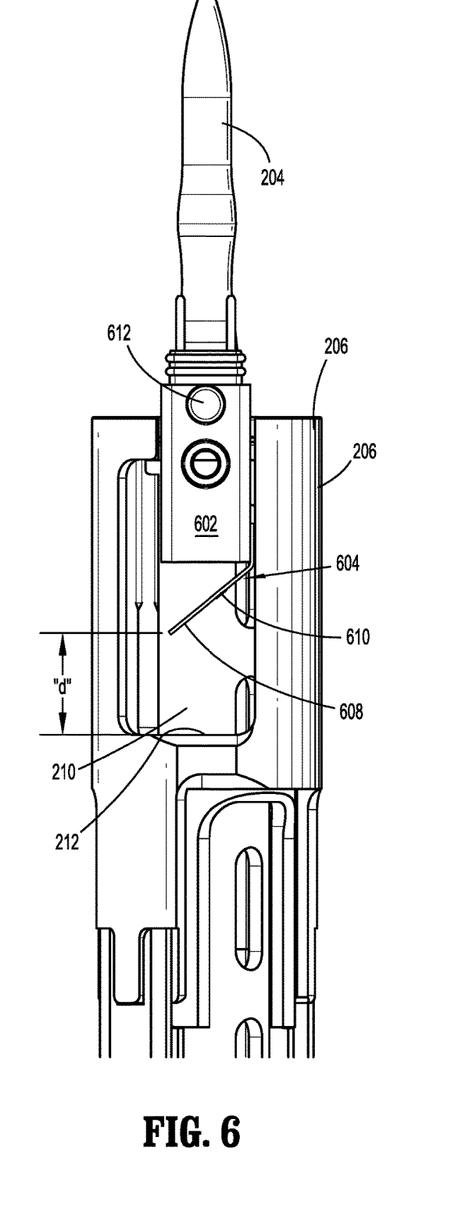
FIG. 6 is a side elevation view of the distal end of the elongate tool illustrating the pusher in an initial position relative to the linear position sensor.
Figure 7:
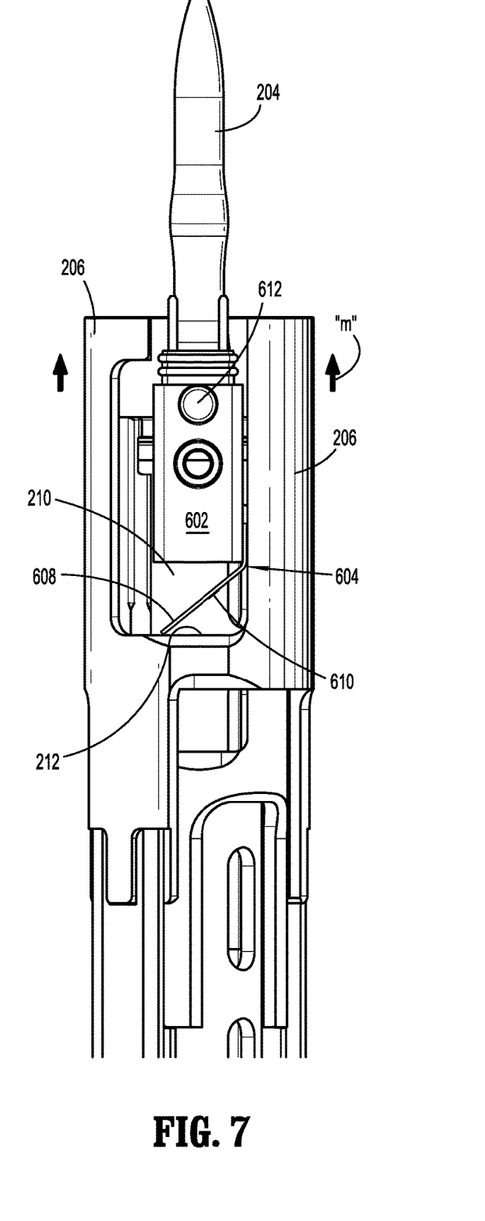
FIG. 7 is a view similar to the view of FIG. 6 illustrating the pusher engaging the linear position sensor during the firing stroke of the pusher.

The fastener apparatus 10 is activated via one or more of the actuator 104, 106, 108 causing activation of the motor 400, approximating movement of the anvil 304 and the fastener cartridge 302, and initiation of the pusher 206 through a firing stroke "m". The pusher 206 advances from the initial position depicted in FIG. 6 to the position of FIG. 7 where the sensor contact surface 212 of the pusher 206 contacts the spring 608 of the linear position sensor 604. In FIGS. 6-7, the outer body 202 of the elongate tool 200 and the anvil 304 of the end effector 300 are removed for illustrative purposes. As indicated hereinabove, the pusher 206 may freely travel a distance "d" (FIG. 6) prior to contact of the sensor contact surface 212 with the linear position sensor 604 due to manufacturing tolerances, dimensioning of the internal components of the elongate tool 200 utilized for the procedure, etc.

Figure 8:
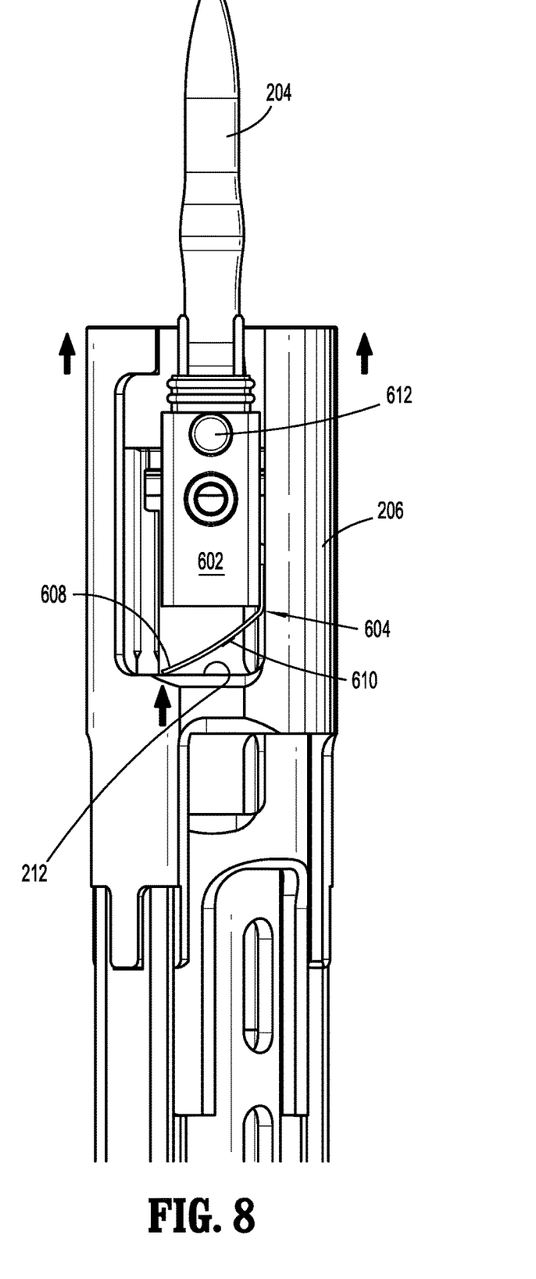
FIG. 8 is a view similar to the view of FIG. 7 illustrating the pusher exerting a force on the linear position sensor during continued movement through the firing stroke.
Figure 9:
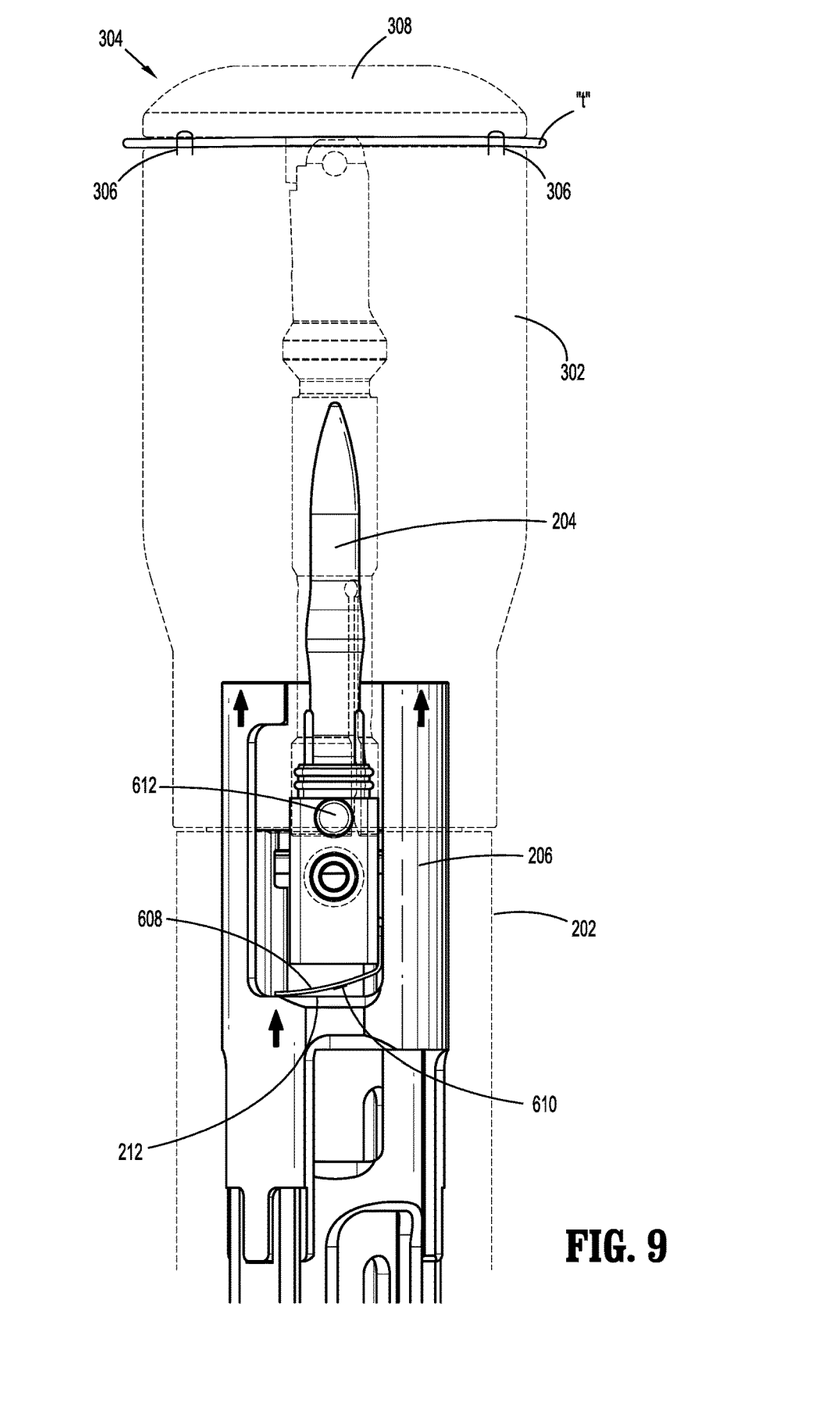
FIG. 9 is a side elevation view similar to the view of FIG. 6 with the end effector of the elongate tool shown in phantom illustrating the pusher and the linear position sensor upon completion of the firing stroke.

With reference to FIG. 8, continued advancing movement of the pusher 206 through the firing stroke causes the sensor contact surface 212 of the pusher 206 to engage and bend the spring 608 of the linear position sensor 604 thereby subjecting the strain gauge 610 to increased strain. The strain gauge 610 sends at least one output signal 610s (FIG. 1) to the controller 500 representative of the degree of strain or force to which it is subjected. The data associated with the output signal 610s sent by the strain gauge 610 is compared with the calibration data 506 in memory 502, which is interpreted by the software or logic of the controller 500, to provide the clinician with an accurate representation of the location of the pusher 206. The location of the pusher 206 may be represented on the visual display 508 in the form of alpha-numeric symbols, charts, graphs or any other indicia. Continued movement of the pusher 206 exerts greater force or strain on the strain gauge 610 (or in the event the pusher is retracted 206, less strain on the strain gauge 610) which is communicated to via additional output signal(s) 610s, and processed, by the controller 500 thereby providing the clinician with continuous confirmation of the location of the pusher 206. Upon detection of a strain corresponding to completion of the firing stroke by the pusher 206, the clinician is apprised via the controller 500 and/or the visual display 508. FIG. 9 illustrates completion of the firing stroke of the pusher 206.

In FIG. 9, the fastener cartridge 302 and the anvil 304 are depicted (in phantom) in the approximated condition, which may be effected by operation of the motor 400 in accordance with a sequence or program within the logic of the controller 500. Commonly assigned U.S. Provisional Application No. 62/066,518 to Cabrera et al., filed Oct. 21, 2014, the entire contents of which disclosure are incorporated by reference herein, discloses mechanism(s), in conjunction with a powered handle, for moving the fastener cartridge 302 and the anvil 304 between open and approximated conditions, and for advancing a fastener pusher assembly. See also U.S. Patent Publication No. 2011/0121049 to Malinouskas et al., U.S. Patent Publication No. 2013/0214025 to Zemlok et al. and/or U.S. Patent Publication No. 2015/0014393 to Milliman, previously incorporated by reference herein. Alternatively, the fastener cartridge 302 and the anvil 304 may be approximated by one or more mechanical levers, manually manipulative members, etc. associated with the handle 200. The fasteners or staples 306 are depicted fired from the fastener cartridge 302 to pass through tissue "t" and crimped by the anvil head 308 of the anvil 304.

During the firing stroke, the controller 500 and associated logic may analyze or interpret the output signals 610s, 612s (FIG. 1) from the linear position sensor 604 and/or the feedback sensor 612, respectively, and control or alter functioning of the motor 400 including changing the velocity of the firing stroke of the pusher 206 via control of the motor 400, reverse movement of the motor 400 and the pusher 206, alter the distance of the firing stroke of the pusher 206 and/or halt operation of the motor 400.

Figure 10:
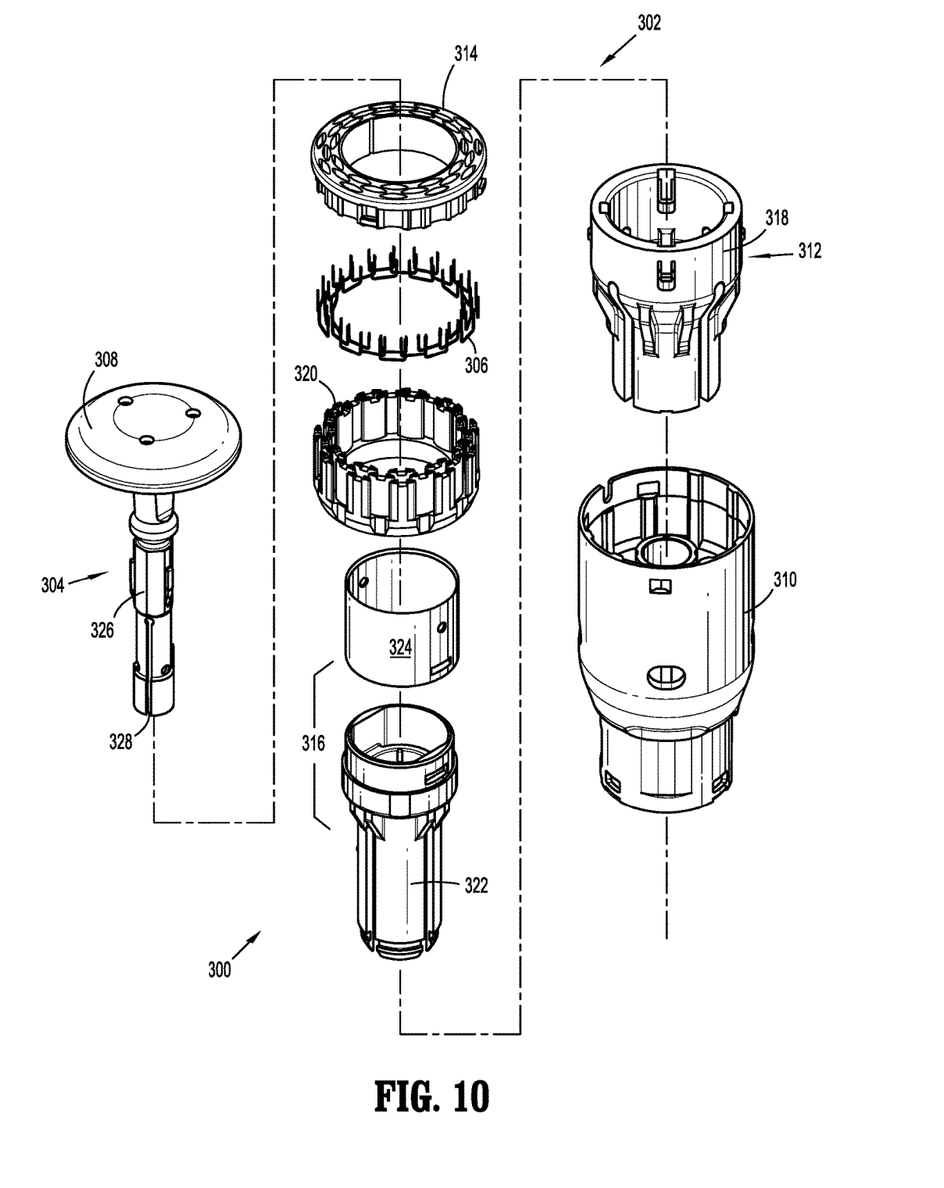
FIG. 10 is an exploded perspective view illustrating exemplative components of the end effector.

FIG. 10 illustrates exemplative components of one suitable end effector 300 for use with the fastener apparatus 10. The fastener cartridge 302 of the end effector 300 includes a housing 310, a pusher assembly 312, a fastener holder 314, and a knife assembly 316. The pusher assembly 312 includes a pusher adapter 318 and a pusher member 320, which couples, through any conventional arrangement, with the pusher 206 extending within the outer body 202 of the elongate tool 200. The knife assembly 316 includes a knife carrier 322 and a circular knife 324, which also may be operatively coupled to the pusher 206. The fastener holder 314 includes a plurality of fasteners or staples 306. The anvil 304 of the end effector 300 includes an anvil shaft 326 which defines a longitudinal bore 328 for at least partial reception of the anvil retainer 204 (FIG. 2). When positioned within the longitudinal bore 328, the anvil retainer 204 and the anvil 304 are coupled to each other. The anvil 304 includes the circular anvil head 308 with pockets (not shown) which receive and crimp the fasteners or staples 306 ejected by the fastener holder 314.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A fastener apparatus, which comprises:
   a handle;
   an elongate body connected to the handle, the elongate body defining a longitudinal axis and having proximal and distal ends;
   a fastener cartridge disposed adjacent the distal end of the elongate body, the fastener cartridge having at least one fastener;
   a pusher at least partially disposed within the elongate body, the pusher adapted for longitudinal movement through a firing stroke to eject the at least one fastener from the fastener cartridge;
   a linear position sensor mounted within the elongate body and dimensioned and positioned to engage the pusher during movement through the firing stroke, the linear position sensor including a sensor mount, and a spring supported in cantilevered fashion in relation to the sensor mount and positioned to be engaged by the pusher, the linear position sensor adapted to send at least one output signal representative of strain imparted thereupon by the pusher during the firing stroke; and
   a controller configured and adapted to determine a position of the pusher within the firing stroke based upon the at least one output signal.

2. The fastener apparatus according to claim 1 including a visual display for displaying visual indicia corresponding to the position of the pusher during the firing stroke.

3. The fastener apparatus according to claim 1 wherein the fastener cartridge includes a plurality of fasteners arranged in an annular array and further including an anvil mountable relative to the fastener cartridge, the anvil including an anvil head dimensioned for forming the fasteners.

4. A fastener apparatus, which comprises:
a handle;
an elongate body connected to the handle, the elongate body defining a longitudinal axis and having proximal and distal ends;
a fastener cartridge disposed adjacent the distal end of the elongate body, the fastener cartridge having at least one fastener;
a pusher at least partially disposed within the elongate body, the pusher adapted for longitudinal movement through a firing stroke to eject the at least one fastener from the fastener cartridge;
a linear position sensor mounted within the elongate body and dimensioned and positioned to engage the pusher during movement through the firing stroke, the linear position sensor adapted to send at least one output signal representative of strain imparted thereupon by the pusher during the firing stroke; and
a controller configured and adapted to determine a position of the pusher within the firing stroke based upon the at least one output signal,
wherein the controller includes a memory for storing calibration data associated with the strain imparted on the linear position sensor by the pusher at a plurality of positions of the pusher during the firing stroke.

5. The fastener apparatus according to claim 4 wherein the controller is configured to compare the at least one output signal to the calibration data to determine the position of the pusher within the firing stroke.

6. The fastener apparatus according to claim 4 wherein the linear position sensor includes a spring member dimensioned to be engaged by the pusher during movement through the firing stroke and a strain gauge mounted to the spring member, the strain gauge adapted to send the at least one output signal.

7. The fastener apparatus according to claim 6 wherein the spring member is a leaf spring mounted within the elongate body in cantilever relation.

8. The fastener apparatus according to claim 6 wherein the pusher includes a sensor contact surface for engaging the spring member, the sensor contact surface positioned to engage the spring member upon movement of the pusher during the firing stroke.

9. The fastener apparatus according to claim 4 including a motor operably coupled to the pusher for controlling movement of the pusher.

10. The fastener apparatus according to claim 9 wherein the controller is configured to control operation of the motor based upon the at least one output signal sent by the linear position sensor.

11. The fastener apparatus according to claim 10 including an input device to provide input data for storing by the memory, the input data including one of the calibration data, a size of the at least one fastener, tissue type or biographical data of a subject.

12. The fastener apparatus according to claim 11 wherein the controller is configured to control at least one parameter of operation of the motor based upon the input data.

13. The fastener apparatus according to claim 9 including at least one feedback sensor to monitor a load condition of the motor.

14. A sensor assembly for use with a surgical apparatus of the type including at least one pusher adapted to travel through a firing stroke, the sensor assembly comprising:
a linear position sensor mountable within the surgical apparatus and being dimensioned and positioned to engage the pusher during movement through the firing stroke, the linear position sensor adapted to send at least one output signal representative of strain imparted thereupon by the pusher during the firing stroke; and
a controller configured and adapted to determine a position of the pusher within the firing stroke based upon the at least one output signal and calibration data stored within memory of the controller.

15. The sensor assembly according to claim 14 wherein the linear position sensor includes a spring member dimensioned to be engaged by the pusher during movement through the firing stroke and a strain gauge mounted to the spring member, the strain gauge adapted to send the at least one output signal.

* * * * *